United States Patent [19]

Klearman et al.

[11] Patent Number: 5,665,059
[45] Date of Patent: Sep. 9, 1997

[54] PIVOTALLY ADJUSTABLE SELF-SUPPORTING FOOT ORTHOSIS

[75] Inventors: Jeffrey D. Klearman; Robert Bronson, both of St. Louis; Jerry M. Roth, House Springs, all of Mo.

[73] Assignee: Therapy Concepts, Inc., St. Louis, Mo.

[21] Appl. No.: 534,662

[22] Filed: Sep. 27, 1995

Related U.S. Application Data

[63] Continuation-in-part of Ser. No. 324,723, Oct. 18, 1994, Pat. No. 5,571,037.

[51] Int. Cl.[6] ............................................. A61F 5/00
[52] U.S. Cl. ........................... 602/27; 128/887; 602/16
[58] Field of Search .................... 602/5, 16, 20, 602/23, 27–29; 128/845, 882; 36/110, 117, 120

[56] References Cited

U.S. PATENT DOCUMENTS

| | | |
|---|---|---|
| 4,076,022 | 2/1978 | Walker . |
| 4,955,149 | 9/1990 | Ottieri . |
| 4,998,537 | 3/1991 | Rau . |
| 5,020,523 | 6/1991 | Bodine . |
| 5,022,390 | 6/1991 | Whiteside . |
| 5,088,479 | 2/1992 | Detoro . |
| 5,151,081 | 9/1992 | Williams . |
| 5,154,695 | 10/1992 | Farris et al. . |
| 5,224,925 | 7/1993 | Varn ............................ 602/27 X |
| 5,298,013 | 3/1994 | Lonardo ........................ 602/27 X |
| 5,328,444 | 7/1994 | Whiteside ..................... 602/27 X |
| 5,367,789 | 11/1994 | Lamont ........................ 602/28 X |
| 5,370,604 | 12/1994 | Bernardoni . |
| 5,431,624 | 7/1995 | Saxton et al. ................. 602/27 |
| 5,453,082 | 9/1995 | Lamont ........................ 602/27 |
| 5,486,157 | 1/1996 | DiBenedetto .................. 602/27 |
| 5,542,912 | 8/1996 | Hess ........................... 602/27 |
| 5,545,127 | 8/1996 | DeToro ........................ 602/27 |

OTHER PUBLICATIONS

Oscar Plus Ankle/Foot Orthosis by OCS, Orthosis Corrective Systems, Inc., tri-fold brohure and Care Plan sheet.

E-Z Boot™, Therapeutic Orthotic System, Medi-Key™ Medical Products, Inc., two-sided color brochure.

E-Z Boot™, Protocol for the Therapeutic Food and Leg Orthotic System, Jan. 1, 1991, 7-page explanation and assessment.

Primary Examiner—Linda C. Dvorak
Attorney, Agent, or Firm—Howell & Haferkamp, L.C.

[57] ABSTRACT

An ankle/foot orthosis for supporting a patient's ankle in a neutral orientation, including a calf section and a foot section pivotally coupled to the calf section to allow adjustment of a relative angle therebetween. A brace extends between the backsides of the foot and calf sections for maintaining the relative angle in a fixed position, and for allowing adjustment of the orthosis into one of several predetermined positions including an upright position, a fully reclined position, and one or more intermediate positions. The foot section includes a heel portion that maintains positive clearance with a patient's heel, which is an ulcer prominent area, and prevents inadvertent contact therewith, particularly when the orthosis is in the upright position. In the fully reclined position, the orthosis provides access to the patient's heel and sole regions, and elevates the patient's leg and foot above a supporting surface.

23 Claims, 9 Drawing Sheets

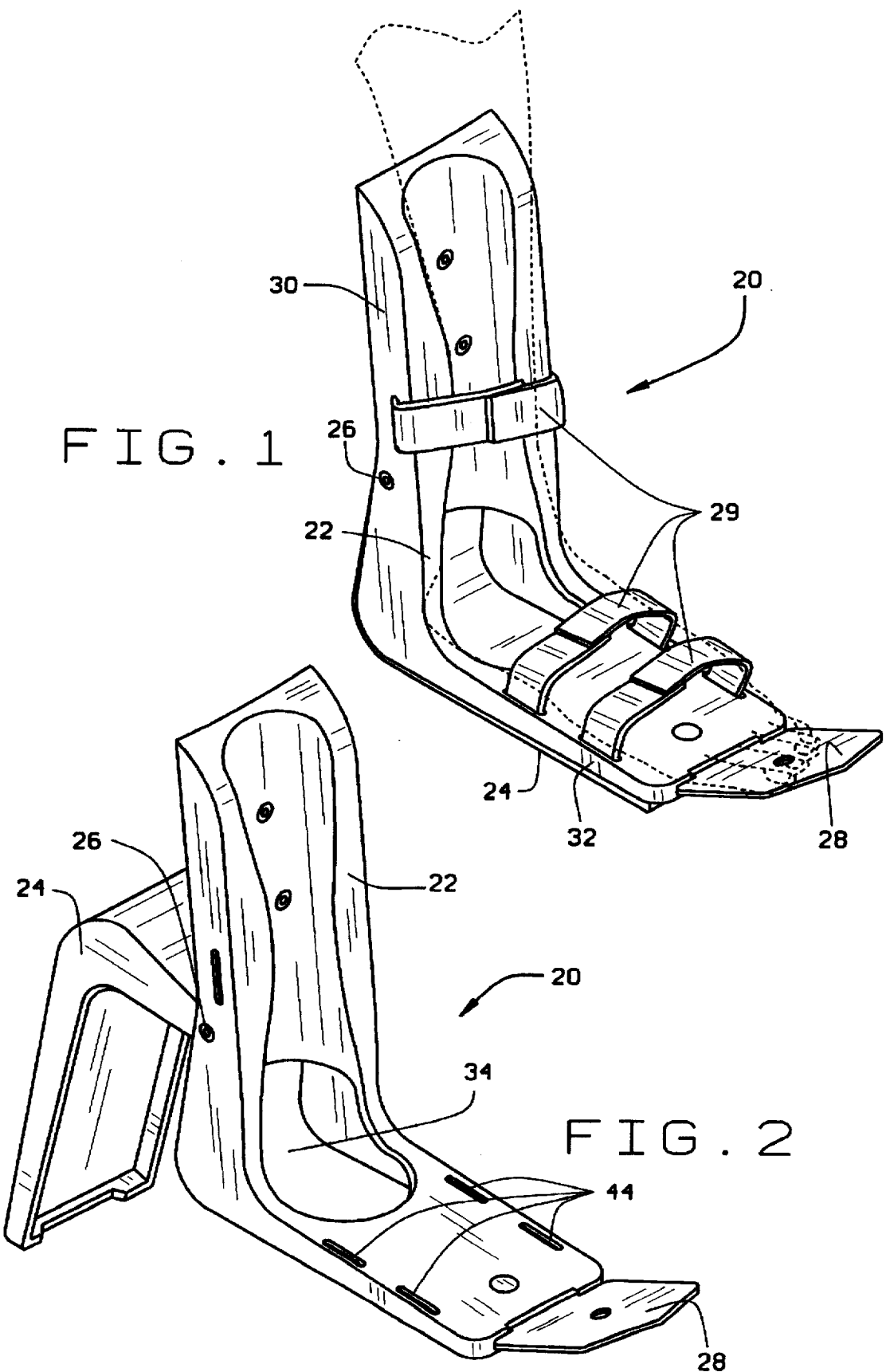

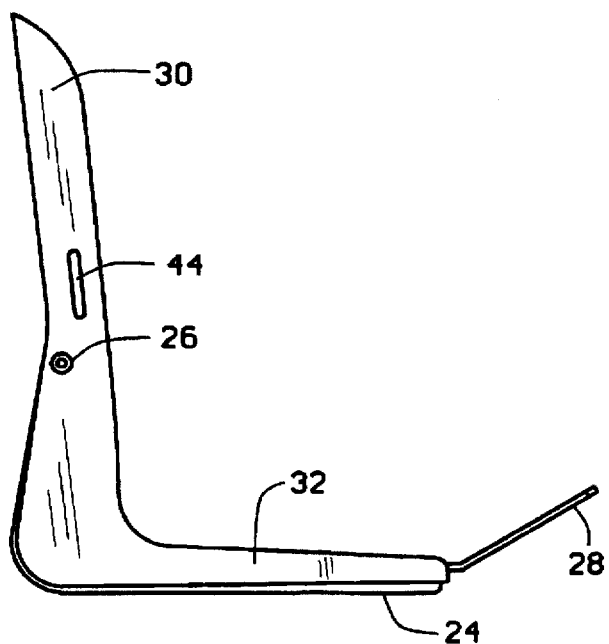
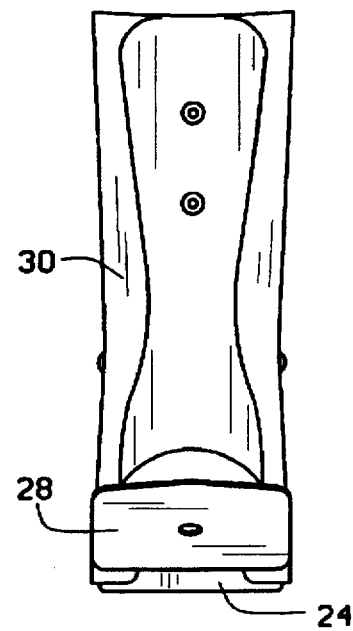
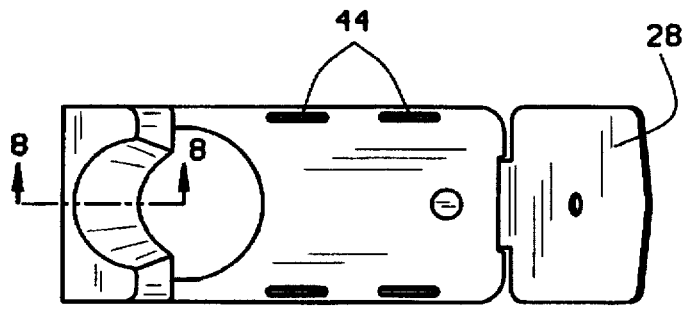
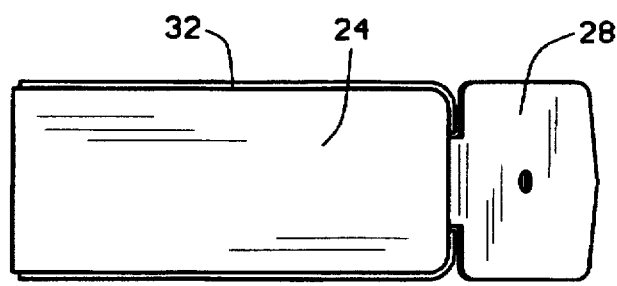
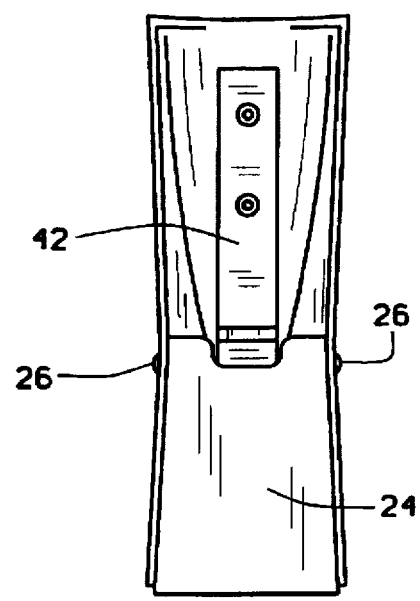
FIG. 3
FIG. 6
FIG. 4
FIG. 7
FIG. 5

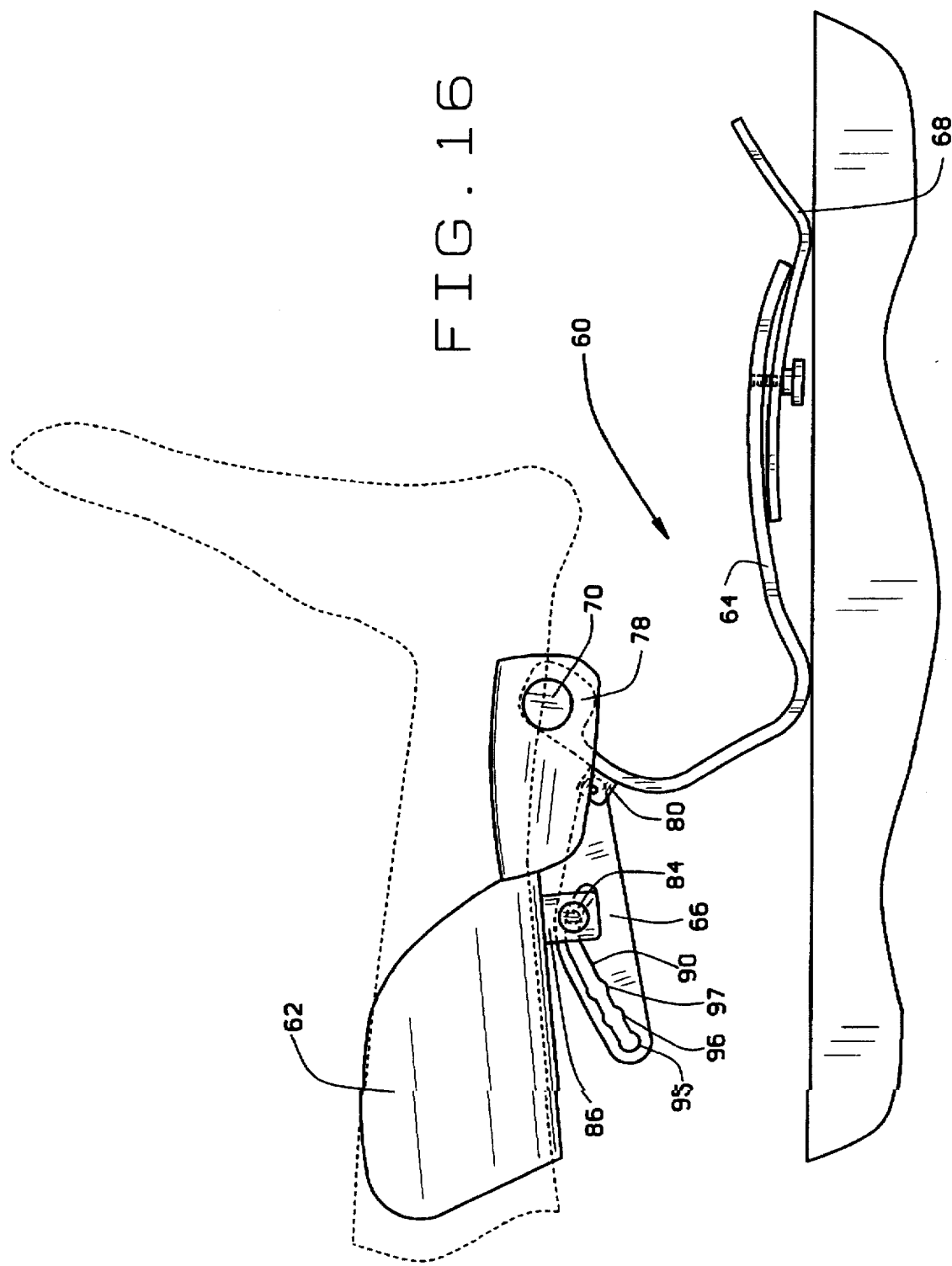

PIVOTALLY ADJUSTABLE SELF-SUPPORTING FOOT ORTHOSIS

This application is a continuation-in-part of application Ser. No. 08/324,723 filed Oct. 18, 1994, now U.S. Pat. No. 5,571,077.

BACKGROUND AND SUMMARY OF THE INVENTION

The problem of decubitus ulcers and blisters experienced by people suffering from foot-drop and other nonambulatory conditions is well documented. The primary cause of these ulcers is the immobility of the bedridden patient which causes an interruption in the flow of blood to capillaries in areas of the skin adjacent bone protuberances. The interruption of blood flow to the capillaries causes skin cells to die which results in a breakdown of skin tissue and the development of ulcers. The heel is an area particularly susceptible to decubitus ulcers.

Various ankle/foot orthoses and splints are known in the art for supporting, aligning and correcting foot deformities. For instance, a splint may he chosen for a severely sprained foot or ankle which protects and immobilizes the ankle joint in proper alignment to facilitate healing. Further, persons suffering from paralysis of the anterior leg muscles resulting in insufficient voluntary ankle dorsiflexion (commonly referred to as foot-drop) may select an ankle/foot orthosis which maintains the ankle joint in a neutral position and supports the toes while the person is bedridden and/or during walking. While these prior art splints and orthoses adequately support and align the ankle and/or foot, these devices do not address other problems frequently experienced by nonambulatory patients, or patients suffering from foot-drop and other ankle/foot ailments. Nor do these prior art devices provide access for treating (applying ointments or changing dressings) any ulcers without removing the splint/orthosis. Removing the splint/orthosis each time an ulcer is treated is a time consuming procedure and can he quite painful to these patients whose ankle regions are often aggravated and sore. Moreover, because these prior art devices are designed with the singular intention to physically support and align the ankle region, these splints and orthoses often directly contact and become adhered to the ulcerous area thereby irritating the wound.

Another problem with these prior art devices is that they fail to provide a convenient means for elevating the foot. Elevating an injured extremity is a proven technique to minimize swelling, increase blood circulation, and facilitate the healing process. Several of the prior art splints/orthoses include a mechanism to couple with a traction device thereby enabling elevation of the foot. It is also known to elevate the foot by placing pillows, towels, or books beneath the foot. However, neither of these prior art techniques are convenient for a non-ambulatory person. The former requires specialized traction equipment which is often unavailable except in a hospital setting. Further, spare pillows, books, towels, and other support materials may become undesirably soiled, can be uncomfortable unless care is taken to continuously adjust their positioning, and require a non-ambulatory patient to "ambulate" to fetch the materials or else receive constant attention from others.

In order to solve these and other problems in the prior art, the inventors herein have succeeded in designing and developing orthoses for supporting a patient's ankle in a neutral position while enabling access for treatment of ulcers on the heel or foot bottom. As used herein "orthosis" shall refer to any device employed to support or align the foot, to prevent or correct foot deformities, or to improve the functions of the foot. Orthoses specifically include splints. An orthosis according to a first embodiment of the present invention includes a generally "L" shaped frame which is fitted to a patient's foot and back ankle, and is secured with Velcro® hook and loop straps, tape, or other suitable securing means wrapped around the patient's leg. The frame includes at least one aperture located at the patient's heel such that access to this ulcer prominent region is not obstructed by the frame. A pivotally coupled cover over the aperture protects any ulcers on the heel from inadvertent contact when closed. By rotating the cover about its pivot, the cover may be swung open to expose the patient's heel thereby allowing treatment of the ulcer without disturbing the frame secured to the patient's leg. This eliminates the time consuming, and often painful, removal of the orthosis as required by the prior art to treat the ulcer. As used herein, "closed" shall refer to the cover positioned adjacent the aperture and "open" shall refer to the cover swung away from the aperture.

Moreover, a spring biased cover latch mounted to the frame allows the cover to be locked in an over-center open position for resting the patient's foot with the cover supporting it above any convenient resting surface, such as a bed. Special traction equipment and pillows/books are no longer necessary to elevate a patient's foot as with the prior art. Opening and closing the cover is easily performed by a patient by simply reaching down to the orthosis, operating the cover latch (to open), and rotating the cover about its pivot.

An orthosis according to another embodiment of the present invention includes a pivotally adjustable frame comprising a foot section and a calf section that are fitted to a patient's foot and calf regions, respectively, and are secured to the patient with Velcro® hook and loop straps or other suitable means wrapped around the patient's foot and calf regions. The foot section is pivotally coupled to the calf section so as to allow adjustment of a relative angle therebetween.

In this embodiment of the invention, a brace extends between the foot and calf sections for maintaining the relative angle in a fixed position, and for allowing adjustment of the orthosis to one of several predetermined positions. The brace is pivotally connected to the foot section and is adjustably connected to the calf section through an elongated slot extending through the brace and several eyelets disposed about the elongated slot. A latch extends through a bracket connected to the calf section, through the elongated slot, and through one of the eyelets when the latch is in a "locked" position so as to adjustably connect the brace to the calf section while maintaining the relative angle between the foot and calf sections in a fixed position and preventing collapse of the orthosis.

When an adjustment button is depressed, the latch is moved to an "unlock" position and can slide along the elongated slot to allow adjustment of the relative angle between the foot and calf sections. In an "upright" or approximately 90 degree position, the orthosis supports the patient's ankle in a neutral orientation while preventing inadvertent contact with the patient's heel. The foot section includes a heel portion that is configured to maintain positive clearance between the patient's heel and the foot section.

In a "fully reclined" position of the orthosis with the patient's leg in a generally horizontal position, the patient's heel and sole are exposed to allow treatment thereof without removing the orthosis from the patient's leg. Moreover, in the fully reclined position, the patient's leg can rest in the calf section with the foot section elevating the calf section, and the patient's leg and foot supported thereby, above any convenient resting surface. The orthosis can also be adjusted for comfort to positions intermediate the upright and fully reclined positions.

Thus, the present invention satisfies a long-felt need by providing an orthosis which can sturdily support an ankle while at the same time allowing heel and foot ulcers to be treated without removing the orthosis, and which provides a stable and convenient mechanism to elevate the foot. While the principal advantages and features of the present invention are briefly described above, a more thorough understanding and appreciation for the advantages and features of the invention may be obtained by referring to the drawings and descriptions of the preferred embodiments which follow.

BRIEF DESCRIPTION OF THE DRAWINGS

FIG. 1 is an isometric view of an orthosis according to a first embodiment of the present invention as applied to a patient's foot (illustrated in phantom);

FIG. 2 is an isometric view of the orthosis of

FIG. 1 illustrating the cover latched in an over-center open position;

FIG. 3 is a right-side elevation view thereof illustrating the cover closed;

FIG. 4 is a top plan view thereof;

FIG. 5 is a bottom plan view thereof;

FIG. 6 in an front elevation view thereof;

FIG. 7 is a rear elevation view thereof;

FIG. 16 is a side elevation view of the orthosis of FIG. 13 adjusted to a fully reclined position;

DETAILED DESCRIPTION OF THE PREFERRED EMBODIMENTS

Figure 10:
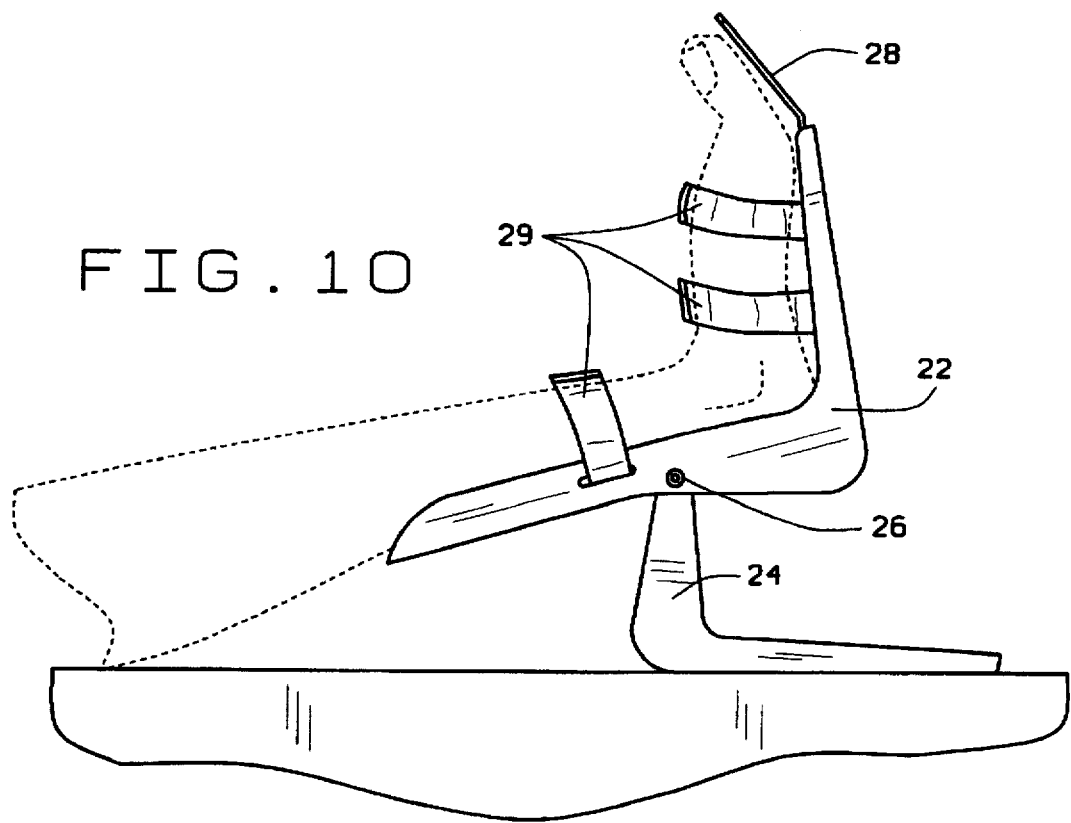
FIG. 10 is a right-side elevation view of the orthosis illustrating the cover locked in an open position elevating a patient's foot illustrated in phantom.

An orthosis constructed according to the principles of the present invention is indicated generally as 20 in FIGS. 1 and 2. The orthosis 20 includes a frame 22, a cover 24 pivotally coupled to the frame at two pivot points 26, an extendable toe platform 28, and a plurality of Velcro® hook and loop straps 29 securing the frame to the patient's leg. (See FIG. 10 for an illustration of straps 29). The term "ankle region" shall herein refer to the portion of a human body from the mid-calf to the toes. The frame is generally "L" shaped having a calf section 30 and a foot section 32 conforming generally to the shape of a human ankle region when the ankle joint is in a neutral position.

Figure 11:
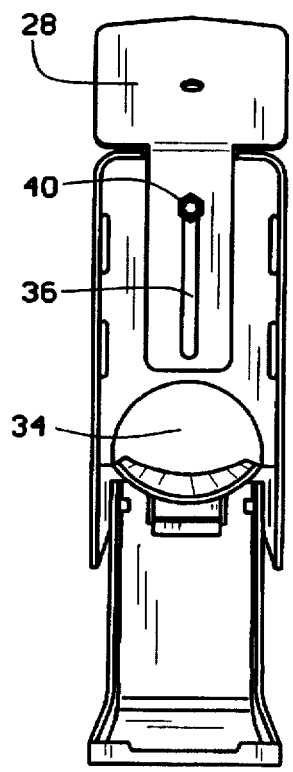
FIG. 11 is a bottom plan view of the orthosis with the cover in an open position illustrating the toe platform in a retracted position.
Figure 12:
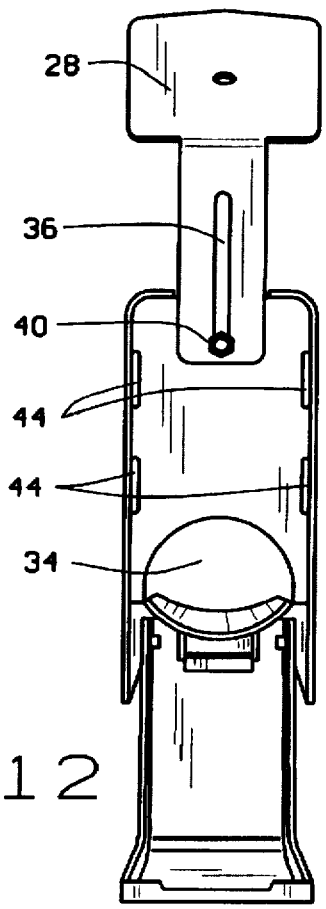
FIG. 12 is a bottom plan view similar to FIG. 11 illustrating the toe platform in a fully extended position.

The anterior of calf section 30 is preferably contoured to the shape of a typical human lower calf and Achilles' tendon. The foot section 32 is preferably flat and extends to the metatarsal heads of a typical human foot. An aperture 34 extends through the frame 22 where the calf section 30 and foot section 32 merge for positioning over a patient's heel when the orthosis 20 is properly secured to the ankle region. The toe platform 28 is mounted to the bottom of the foot section 32 and is adjustable by an elongated slot 36 and a pin 40 to accommodate feet of various lengths (See FIGS. 11 and 12). The platform 28 is angled (relative to the foot section 32) to dorsiflex the toes. Of course, the orthosis 20 may be manufactured in various lengths and widths to readily accommodate a wide range of foot sizes.

Figure 8:
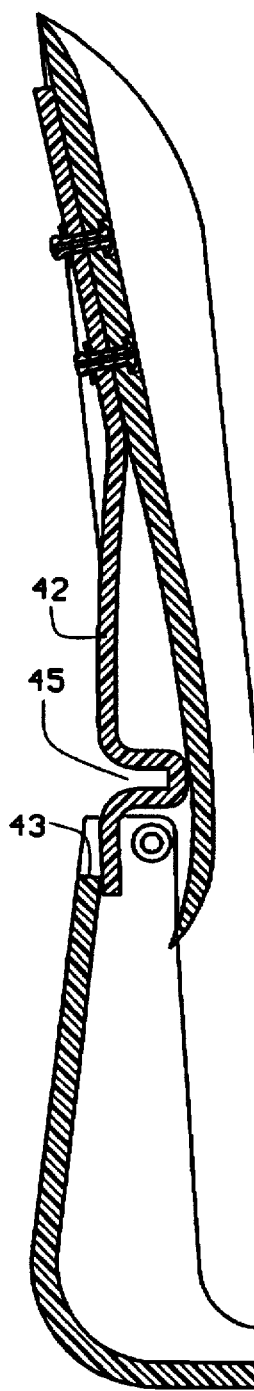
FIG. 8 is a partial cross-sectional view of the orthosis taken along lines 8—8 in FIG. 4.
Figure 9:
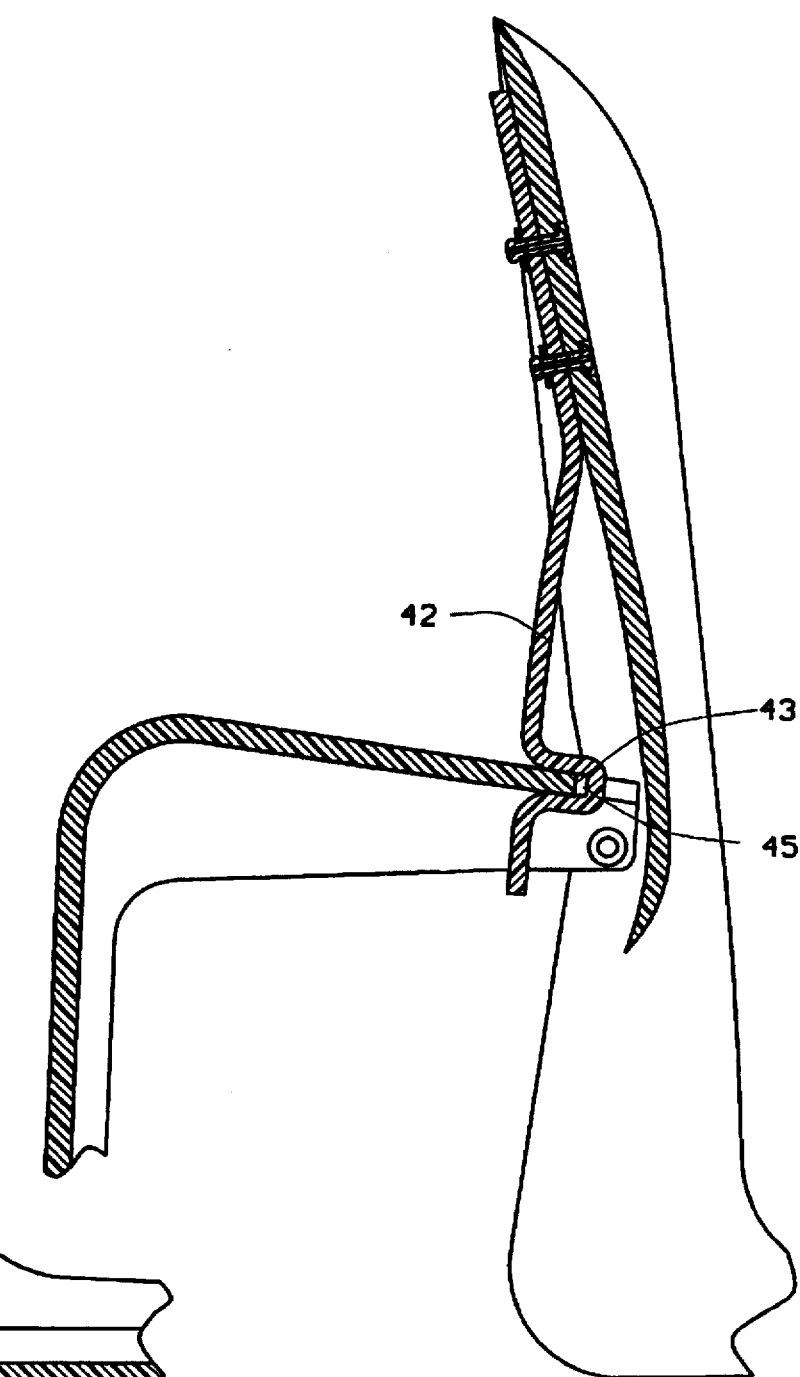
FIG. 9 is a partial cross-sectional view similar to that of FIG. 8 illustrating the cover in a locked over-center open position.

In the preferred embodiment, the cover 24 is generally "L" shaped and, when in the "closed" position, extends from the pivot points 26 over the aperture 34 to the anterior of foot section 32. In this position, the cover is flush with the lateral sides of the calf section 30 and the foot section 32 and is positioned over the aperture thereby protecting any heel ulcers from inadvertent contact. The cover 24 may be rotated about the pivot points 26 to an over-center "open" position wherein the cover 24 is swung away from the aperture. A spring biased cover latch 42 is mounted to the posterior of the calf section 30 to lock the cover 24 in its open position. Locking the cover 24 in the open position provides a sturdy and convenient means for elevating the ankle region. As shown in FIG. 9, the cover 24 may be swung into an over-center open position and locked in place through an upper edge 43 rotating into a groove 45 in cover latch 42. With edge 43 of cover 24 fitting into groove 45 of cover latch 42, the cover 24 is positively secured in an over-center position with respect to its pivot 26. This helps prevent an inadvertent collapsing of the cover 24 as a patient's foot rests in an elevated position with cover 24 resting against a bed or other supporting surface (See FIG. 10). In order to close cover 24 about frame 22, a patient need only depress cover latch 42 to thereby retract groove 45 which frees the upper edge 43 of cover 24 and permits its pivoting about pivot 26 back into a closed position. As explained, the cover 24 is preferably pivotally coupled to the frame 22. However, it is understood that other coupling techniques may be employed which allow the cover to be removed from the aperture without departing from the scope of this invention. For example, the cover 24 may be snap-fit to the frame 22.

Several pairs of slots 44 are spaced about the frame for accepting the straps 29. It is understood that strips of tape or other suitable material may be substituted for the preferred Velcro® hook and loop straps to secure the frame to the ankle region. Notice, the slots 44 about the foot section 32 are preferably located through the top of the foot section 32 such that the straps do not interfere with the opening and closing of the cover 24.

In operation, the orthosis 20 is positioned adjacent the ankle region of a person suffering from foot-drop or another ankle/foot ailment. The orthosis 20 is positioned such that the aperture 34 is over the ulcer prone heel section of the foot. The cover 24 is opened and the extendable foot platform is adjusted according to the length of the person's foot. Velcro® hook and loop straps 29, medical tape, or other suitable straps are placed through the various slot pairs 44 and around the ankle region to thereby securely mount the frame 22 to the ankle region. At this point, the cover 24 is closed thereby covering the aperture 34 and protecting any ulcerous lesions on the heel from inadvertent contact thereby assisting the healing process.

When properly secured to the ankle region, the orthosis 20 supports the ankle region, properly aligns the foot, and maintains the ankle joint in a neutral position much like the orthoses known in the prior art. However, unlike the prior art orthoses, the cover 24 may be opened, thereby exposing the aperture 34 without removing the orthosis frame 22. With the cover in the open position, the heel, and any ulcerous lesions thereon, are easily accessible to a caregiver thereby allowing treatment of the ulcers while the orthosis is secured to the ankle region. Moreover, the cover 24 may be locked in the open position by spring biased latch 42 thereby providing a sturdy mechanism to elevate the foot which is easy to use and convenient for nonambulatory patients. To close the cover, again protecting the ulcer prone heel, the spring biased latch 42 is simply released and the cover 24 is pivoted about the pivot points 26.

In an alternative embodiment, a treaded sole (not illustrated) may be placed on the bottom of the orthosis 20 while the cover 24 is closed thereby facilitating the use of the orthosis 20 as a walking cast. While the aperture 34 is preferably positioned over a patient's heel, it is understood that the aperture may be positioned over the foot bottom and/or various other ankle region locations to facilitate access to ulcerous lesions thereon without departing from the scope of this invention.

Figure 14:
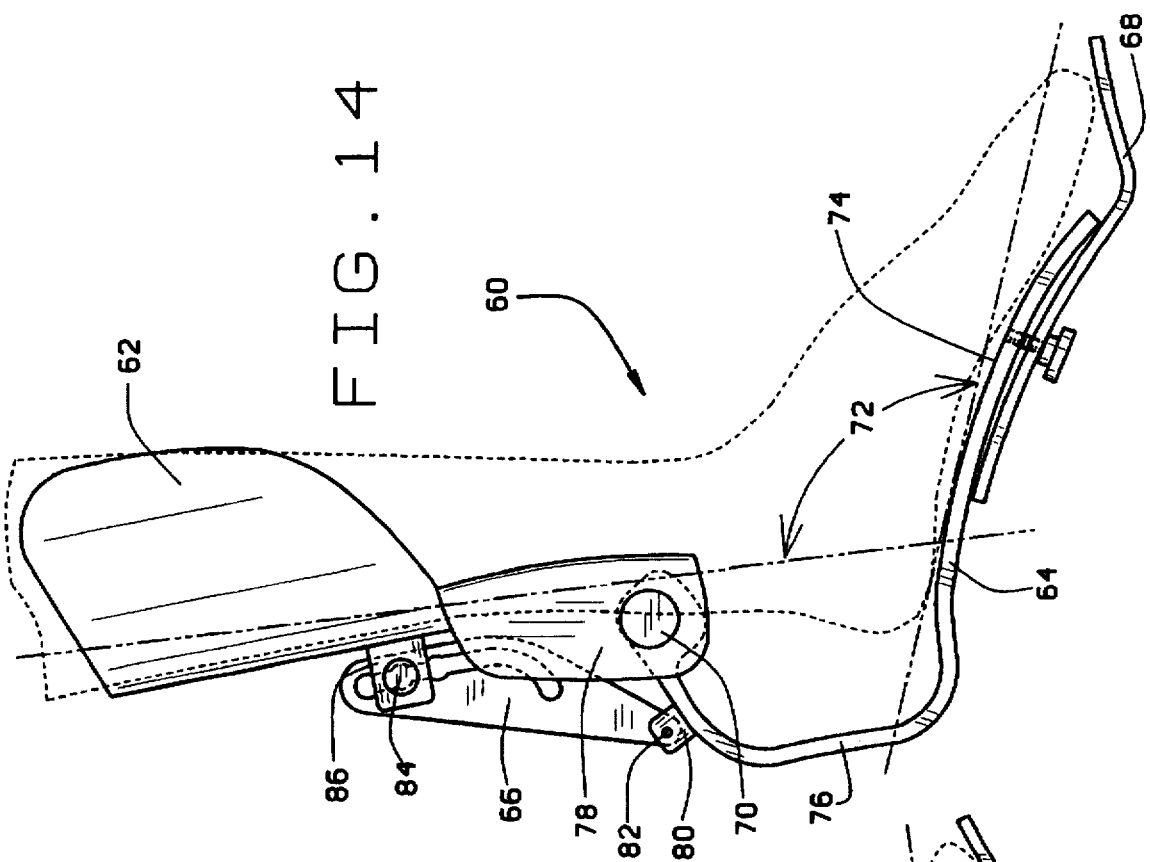
FIG. 14 is a side elevation view of the orthosis of FIG. 13 adjusted to an approximately 110 degree position.
Figure 13:
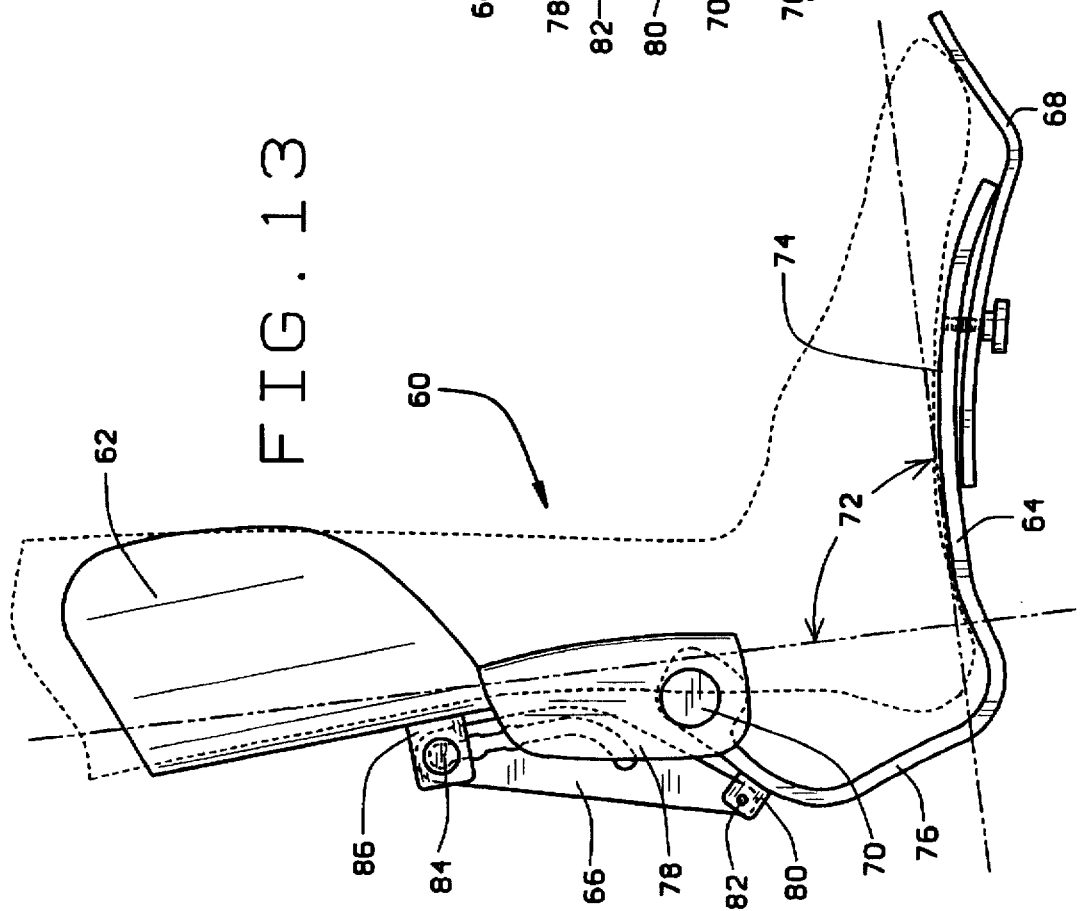
FIG. 13 is a side elevation view of an orthosis according to another embodiment of the present invention as applied in an upright position to a patient's foot (illustrated in phantom)
Figure 17:
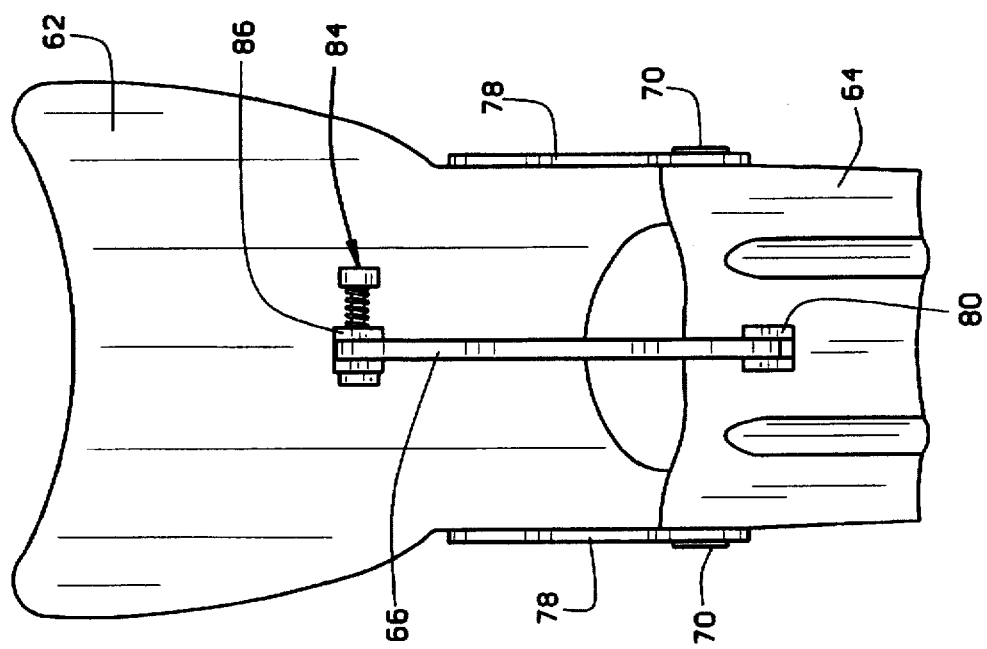
FIG. 17 is a rear elevation view of the orthosis of FIG. 13 in the upright position.
Figure 15:
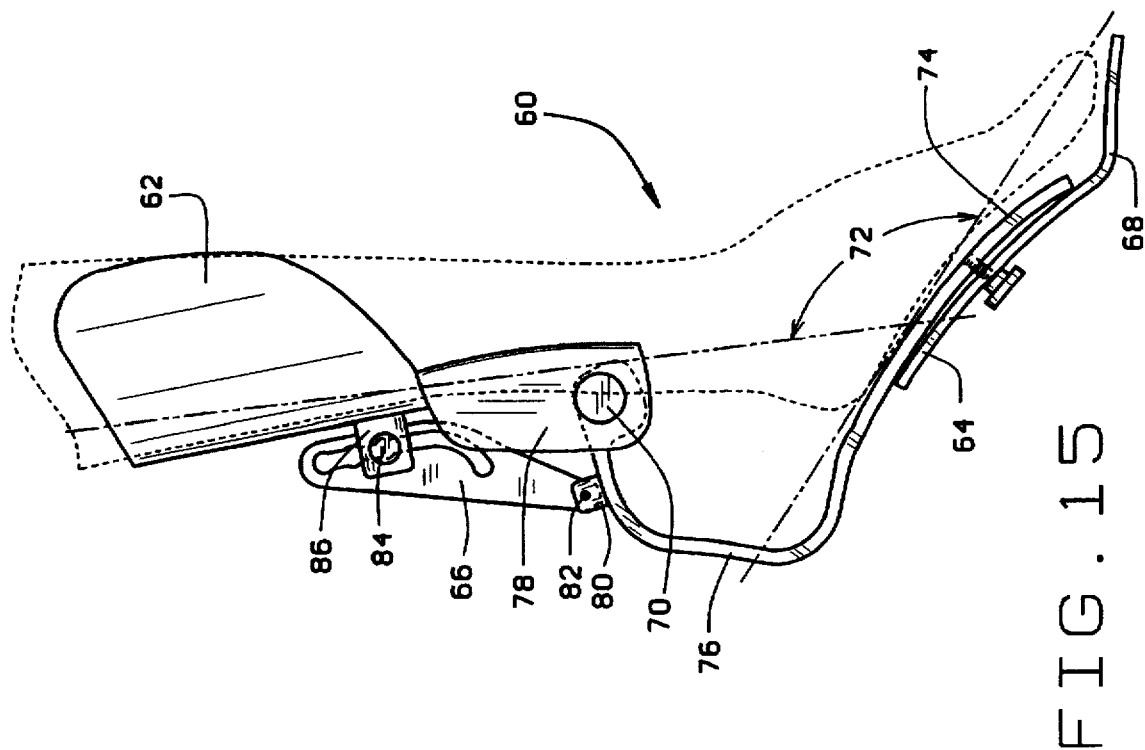
FIG. 15 is a side elevation view of the orthosis of FIG. 13 adjusted to an approximately 130 degree position.

An orthosis constructed according to still another embodiment of the present invention is indicated Generally as 60 in FIGS. 13–16. The orthosis 60 includes a calf section 62, a foot section 64, a brace 66, an extendable toe platform 68, and straps for securing the orthosis to a patient. For illustration purposes, the straps have been omitted from FIGS. 13–16, but will be described in detail below. Foot section 64 is pivotally coupled to calf section 62 at two pivot points 70 to allow adjustment of an angle 72 between the calf section 62 and foot section 64. Angle 72 is taken between two reference planes as shown in FIGS. 13–15. These reference planes are tangential to relative midpoints of the calf section 62 and a sole portion 74 of foot section 64, as illustrated. These reference planes are projections and, hence, may be considered as extending beyond the limits of illustration shown in the figures. For example, as foot section 64 is pivoted about pivot points 70, the intersection between these reference planes extends beyond the envelope of the device, but may still be considered as defining the included angle 72. As the foot section 64 is pivoted to its furthest extent, i.e., to a fully reclined position, the reference planes no longer intersect and instead are parallel but offset. This position is shown in FIG. 16. This fully reclined position may be considered a 180 degree position even though the reference planes are offset from one another and do not intersect. Brace 66 is provided to maintain this relative angle in a fixed position, and to allow selective adjustment of the orthosis into several predetermined positions. Orthosis 60 is shown in FIG. 13 in its upright position.

In this preferred embodiment, brace 66 allows selective adjustment of angle 72 to approximately 90 degrees (FIG. 13), 110 degrees (FIG. 14), and 130 degrees (FIG. 15), as well as adjustment of the orthosis into the fully reclined position, i.e., angle 72 is approximately 180 degrees (FIG. 16), it being understood that other positions and other types of braces can be provided. For example, a brace comprising a threaded rod can be utilized to provide infinite adjustment of the relative angle between the foot and calf sections without departing from the scope of this invention.

Adjusting the orthosis to the fully reclined position provides access to the patient's ankle and sole regions for cleaning or treatment thereof without having to remove the orthosis from the patient, and elevates the patient's leg and foot above a supporting surface, as shown in FIG. 16. Orthosis 60, which is preferably constructed of sturdy ABS polymer plastic, maintains consistent pressure and support on the patient's dorsi/plantar area, and combined with its multi-position capabilities, helps to correct contracture and control foot drop.

Foot section 64 includes the sole portion 74 and a heel portion 76. Sole portion 74 is contoured to the shape of the arch of a typical human sole so as to provide maximum support thereto when the orthosis 60 is secured to a patient. Heel portion 76 is configured such that positive clearance is maintained between the orthosis and the patient's heel region, as shown in FIGS. 13–16. Calf section 62 is contoured to the shape of a typical human lower calf and Achilles' tendon, and includes rearwardly extending flanges 78 to which the foot section 64 is pivotally coupled. Preferably, pivot points 70 comprise plastic pop rivets for pivotally coupling the foot section 64 to calf section 62. Like the previously described embodiment of the present invention, toe platform 68 helps to protect a patient's foot from contact with bed coverings and other objects, is mounted to the bottom of the foot section 64, and is adjustable by an elongated slot and pin to accommodate various lengths of feet.

As shown in FIG. 13, brace 66 is pivotally connected to a lower U-shaped bracket 80 by a pivot pin 82. The lower U-shaped bracket 80 is connected to the foot section 64 on a backside of the heel portion 76 by one or more steel rivets or any other suitable means. An upper U-shaped bracket 86 is attached to the calf section 62 by one or more steel rivets. Brace 66 is adjustably connected to the calf section 62 by a spring biased latch 84 that extends through the upper U-shaped bracket 86 and through a portion of the brace.

Figures 18, 19A, 19B:
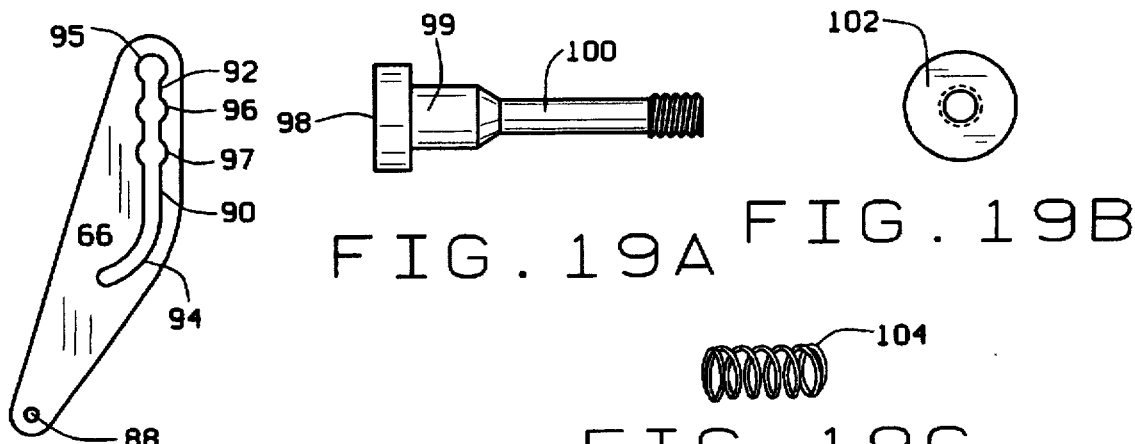
FIG. 18 is a side elevation view of a brace for the orthosis of FIGS. 13–17.
Figure 19C:
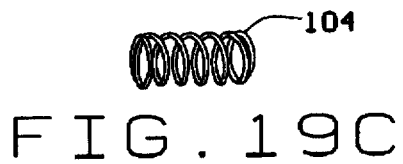
FIG. 19 illustrates the latch components for the orthosis of FIGS. 13–17.

As best illustrated in FIG. 18, brace 66 has a generally triangular configuration and includes an aperture 88 through which pivot pin 82 extends to pivotally connect the brace 66 to the lower U-shaped bracket 80. Brace 66 also includes an elongated slot 90 having a generally straight portion 92 and an arcuate portion 94. Several eyelets 95, 96 and 97 are disposed along the generally straight portion 92 of the elongated slot 90 for adjustably connecting the brace 66 to the calf section 62 to thereby lock the orthosis 60 into one of the predetermined positions. Eyelet 95 corresponds to the upright or 90 degree position shown in FIG. 13, eyelet 96 corresponds to the approximately 110 degree position shown in FIG. 14, and eyelet 97 corresponds to the approximately 130 degree position shown in FIG. 15. Additional eyelets can also be provided so that the orthosis 60 can be locked into additional predetermined positions. For example, an additional eyelet could be provided in the arcuate section 94 of the elongated slot 90 for locking the orthosis into the fully reclined position shown in FIG. 16.

As shown in FIGS. 19A–9C, latch 84 includes a bolt 98, a cylindrical nut 102, and a spring 104. Bolt 98 has a large diameter shank or stop 99, and a small diameter shank or pin 100 for adjustably connecting the brace 66 to the calf section 62. The stop 99 is configured to positively engage one of the eyelets 95–97. When the latch 84 is in the locked position, stop 99 maintains the relative angle between the foot and calf sections, and prevents an inadvertent collapse of the orthosis, particularly when the orthosis is in the fully reclined position. Stop 99 is sized such that it cannot slide through the elongated slot 90. On the other hand, pin 100 of bolt 98 is configured for sliding within the elongated slot 90 of brace 66 when the latch 84 is in an unlocked position to permit adjustment of the orthosis 60 into one of the predetermined positions. The cylindrical nut 102 is utilized for threadedly securing bolt 98 to the upper U-shaped bracket 86 and the brace 66, and functions as an adjustment button for moving the latch 84 from the locked position to the unlocked position.

Figures 20, 21:
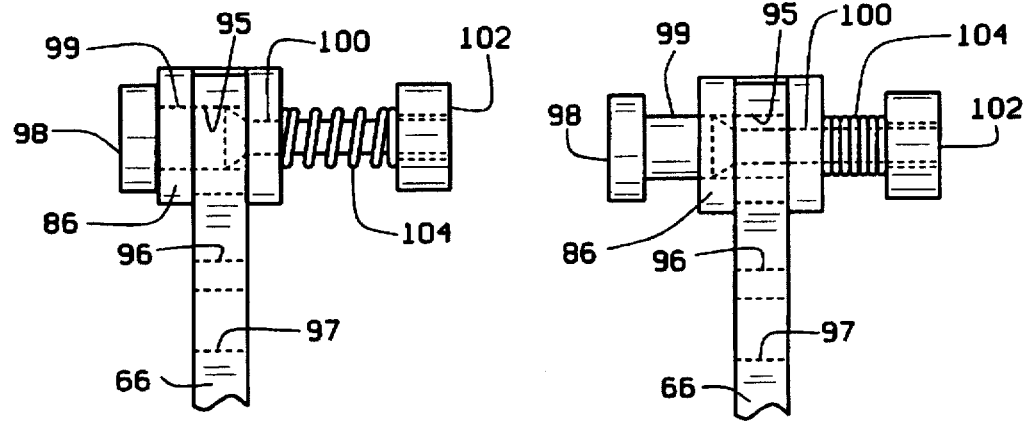
FIG. 20 is a rear elevation view illustrating the latch in a locked position.
FIG. 21 is a rear elevation view illustrating the latch in an unlocked position.

FIG. 20 illustrates the brace 66 adjustably connected to the upper U-shaped bracket 86 with the latch 84 in the locked position. In this illustration, stop 99 extends through and positively engages eyelet 95 to maintain the angle 72 between the foot section 64 and the calf section 62 in the upright position. Spring 104 is positioned about the pin 100 between an outer surface of the upper U-shaped bracket 86 and an inner surface of the cylindrical nut 102 so as to bias latch 84 towards the locked position. Upon depressing the cylindrical nut 102, the stop 99 is displaced away from the brace 66 such that only the pin 100 of bolt 98 extends through the elongated slot 90 and one of the eyelets 95–97. This is the unlocked position, and is shown in FIG. 21. In this position, the pin 100 is free to slide along the elongated slot 90 and allows the orthosis 60 to be adjusted into any one of the predetermined positions. With the latch 84 in the unlocked position, spring 104 is compressed so that latch 84 is biased towards the locked position. If cylindrical nut 102 is no longer depressed, latch 84 will spring back to the locked position upon the alignment of stop 99 with one of the eyelets 95–97.

Figure 22:
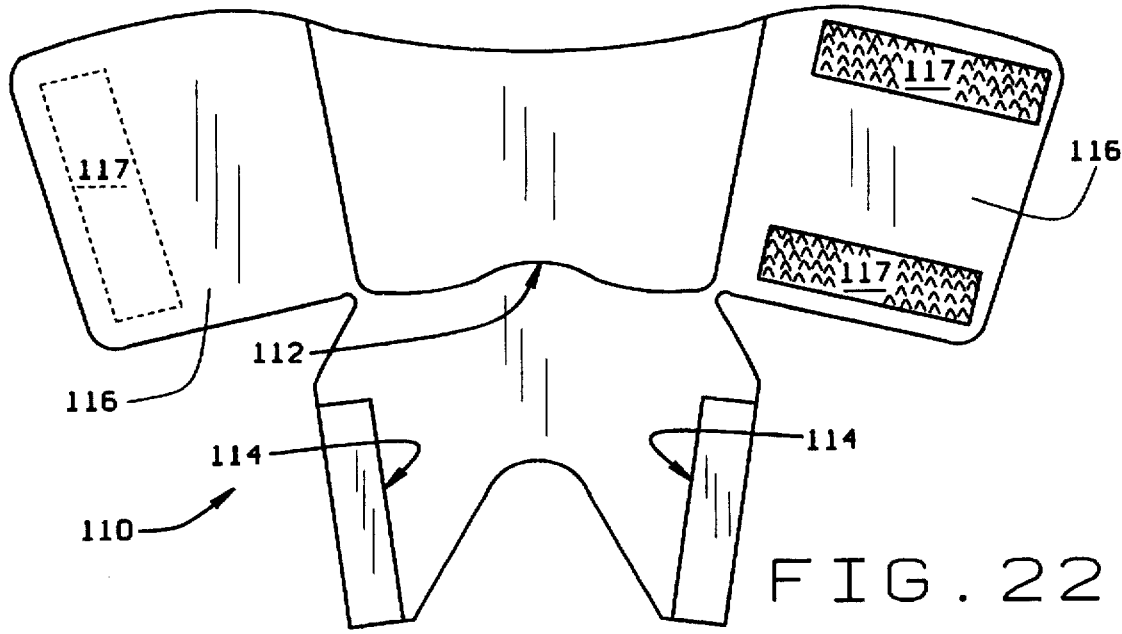
FIG. 22 illustrates a calf closure for securing a patient's calf to the orthosis of FIGS. 13–17.

The orthosis 60 also includes straps for attaching the orthosis to a patient's leg and foot. As shown in FIG. 22, a calf closure 110 is provided for securing the calf section 62 to a patient's calf region. Calf closure 110 includes a large pocket 112 for receiving a top portion of calf section 62 therein, as well as two smaller pockets 114 for receiving the rearwardly extending flanges 78 of calf section 62. Smaller pockets 114 have Velcro® hook and loop tape provided therein for securely attaching the calf closure 110 to the rearwardly extending flanges 78, which also have Velcro® hook and loop tape provided on their interior surfaces. Calf closure 110 includes two leg straps 116 having Velcro® hook and loop tape portions 117 for wrapping around a patient's lower leg and calf region to secure the orthosis 60 to the patient when the calf closure 110 is securely attached to the calf section 62. Calf closure 110 provides maximum support to the patient's calf while preventing the patient's calf from sliding off the orthosis 60 when the orthosis is adjusted to the fully reclined position.

Figure 23:
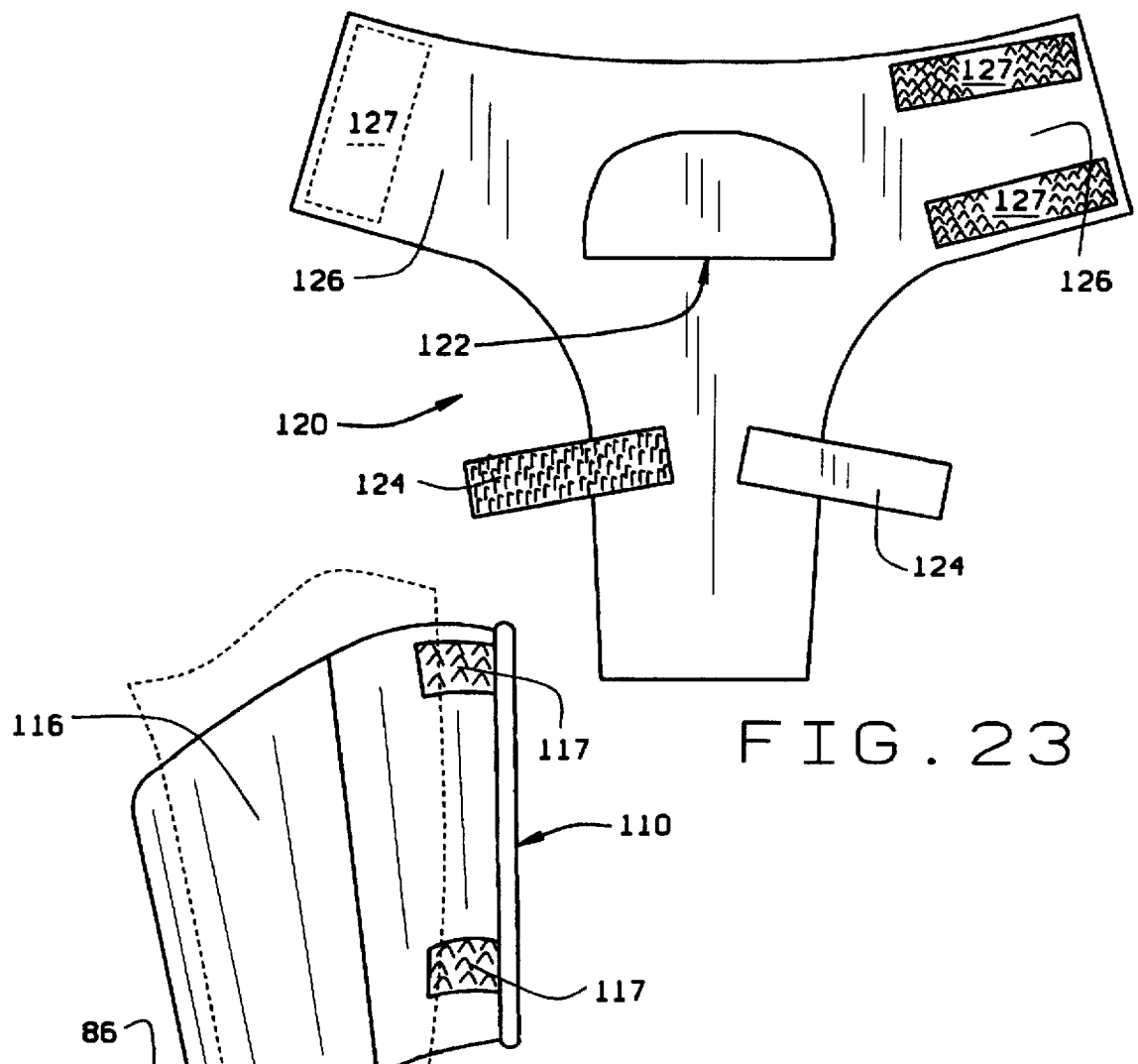
FIG. 23 illustrates a foot closure for securing a patient's foot to the orthosis of FIGS. 13–17.

A foot closure 120 is also provided for securing the foot section 64 to a portion of the patient's foot. As shown in FIG. 23, foot closure 120 includes a pocket 122 for receiving a forward end of foot section 64 therein. Small Velcro® hook and loop straps 124 are also provided for wrapping around a portion of foot section 64 after the forward end of the foot section 64 has been positioned within pocket 122 to releasably attach foot closure 120 to foot section 64. Foot closure 120 also includes foot straps 126 for wrapping around and enclosing a portion of the patient's foot to releasably secure the orthosis 60 to the patient when the foot closure 120 is releasably attached to the foot section 64. Foot straps 126 are also provided with Velcro® tape portions 127 for releasably engaging with one another around a patient's foot.

Figure 24:
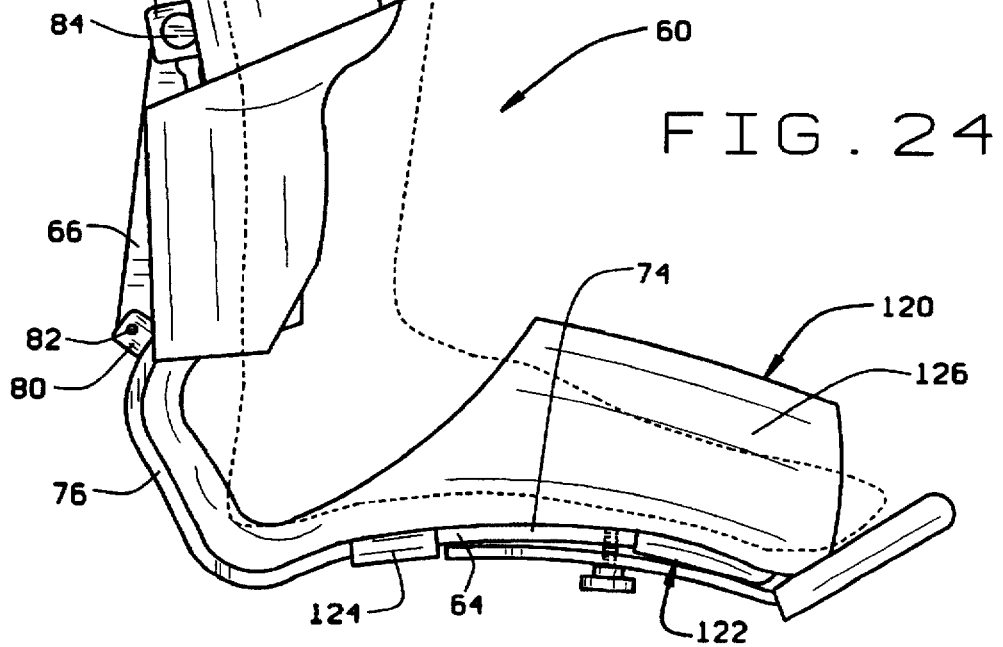
FIG. 24 illustrates the orthosis of FIG. 13 attached to a patient's foot (illustrated in phantom) by the calf and foot closures of FIGS. 22 and 23.

FIG. 24 illustrates the orthosis 60 in the upright position with the calf closure 110 and the foot closure 120 releasably attaching a patient's leg and foot (shown in phantom) to the calf section 62 and foot section 64, respectively. The calf closure 110 and the foot closure 120 completely enclose portions of the patient's calf and foot for providing comfort, for isolating the calf and foot from irritation caused by contact with the calf and foot sections of the orthosis, and for protecting the patient's skin from heat buildup and breakdown. Also illustrated is a toe pad 128 positioned over the adjustable toe platform 68 for providing comfort to the patient's toes. In the preferred embodiment, calf closure 110, foot closure 120, and toe pad 128 are all constructed from soft velvet.

In operation, cylindrical nut 102 can be depressed to move the spring biased latch 84 into the unlocked position, thereby allowing the foot section 64 to be pivoted into a desired predetermined position. Once so positioned, the spring biased latch should be inspected to ensure that it has moved to the locked position, and that stop 99 has engaged one of the eyelets 95–97. A patient's knee is then placed into a bent position, and the foot is firmly positioned on the orthosis with pressure applied over the instep. After the calf closure 110 and foot closure 120 are releasably secured to the calf section 62 and foot section 64 of the orthosis 60, the foot straps 126 are folded around the patient's instep and are secured in place with the Velcro® tape portions 127. The leg straps 116 are then wrapped around the patient's calf and secured in place with the Velcro® tape portions 117. Once attached, the orthosis 60 maintains consistent pressure and support on the patient's dorsi/plantar area, and helps to correct contracture and control foot drop.

If the orthosis is to be adjusted to the fully reclined position for changing dressings on the patient's foot, or for otherwise providing access thereto, or for elevating the patient's leg and foot above a supporting surface, the foot straps 126 are removed from around the patient's instep with the leg straps 116 remaining secured around the patient's calf. Thereafter, cylindrical nut 102 can be depressed to allow the orthosis 60 to be pivoted into the fully reclined position, thereby elevating the patient's leg and foot and providing access to the patient's sole and heel regions for cleaning, treatment, etc. The orthosis 60 can then be pivoted back into the upright position, or one of the intermediate positions, and the foot straps 126 can be refastened around the patient's instep.

In yet another embodiment of the present invention, a laterally extending stabilizing bracket (not shown) is utilized for preventing rolling or turning of the patient's foot from side to side. This stabilizing bracket, or a separate connector bracket, can also be utilized for connecting the orthosis to a complementary bracket on the patient's other foot or leg for controlling the angle and distance of separation of the patient's legs.

Although illustrated embodiments of the present invention are described herein with reference to the accompanying drawings, it is understood that the invention is not limited to those precise embodiments and that various other changes and modifications may be constructed by one skilled in the art without departing from the scope or spirit of the invention. The scope of the invention is defined solely by the claims, and their equivalents, appended hereto.

What is claimed is:

1. An orthosis for supporting a patient's foot in a predetermined orientation, said orthosis including a calf section, a foot section pivotally connected to said calf section to thereby allow adjustment of a relative angle therebetween, and a brace extending between said foot section and said calf section for maintaining said relative angle in a fixed position, said brace having an elongate slot extending therethrough and a plurality of eyelets disposed about said elongate slot, each eyelet corresponding to a different relative angle between said calf and foot sections, said orthosis further comprising a latch adjustably connecting said brace to said calf section by extending through one of said eyelets.

2. The orthosis of claim 1 wherein said foot section includes a heel portion configured to have positive clearance with a patient's heel region when said orthosis is attached to the patient's foot, said brace being connected to the heel portion of said foot section.

3. The orthosis of claim 2 wherein said brace is pivotally connected to the heel portion.

4. The orthosis of claim 1 further comprising a latch for permitting selective adjustment of said orthosis between a first position whereat said foot section contacts the patient's sole and a second position whereat said foot section avoids contact with the patient's sole when said orthosis is attached to the patient's calf.

5. The orthosis of claim 4 wherein said brace has two eyelets extending therethrough, said latch engaging one of said eyelets when said orthosis is in the first position, and said latch engaging the other of said eyelets when said orthosis is in the second position.

6. The orthosis of claim 5 wherein said brace has at least one additional eyelet extending therethrough for selective adjustment of said orthosis into a position intermediate said first and second positions.

7. The orthosis of claim 4 wherein said foot section is pivotally connected to said calf section at a location substantially adjacent to and above the patient's heel when said orthosis is attached to the patient's calf.

8. The orthosis of claim 1 wherein said latch includes a stop for positively engaging one of said eyelets when said latch is in a locked position, and a pin for allowing said latch to slide along said elongated slot when said latch is in an unlocked position.

9. The orthosis of claim 1 wherein said elongate slot includes a generally straight portion and an arcuate portion, said plurality of eyelets being disposed about said generally straight portion.

10. The orthosis of claim 1 wherein said calf and foot sections are configured such that said relative angle can be adjusted from approximately 90 to 180 degrees.

11. The orthosis of claim 1 wherein said foot section is configured such that when said relative angle is adjusted to 180 degrees and said orthosis is attached to the patient's calf, said foot section is separated from the patient's foot in an elevating orientation to allow access to the patient's heel and sole.

12. An orthosis for supporting a patient's foot the orthosis comprising a calf section configured for engaging a calf of the patient, a foot section configured for engaging the patient's foot and operatively connected to the calf section for pivotal movement of the foot section relative to the calf section between first and second positions and a locking mechanism configured for releasably locking the foot section in a plurality of positions between the first and second positions, the locking mechanism being generally rearward of the leg of the patient when the calf section engages the calf of the patient and the foot section engages the foot of the patient, the locking mechanism comprising a brace operatively connected to and moveable with one of said calf section and foot section, and a pin operatively connected to and moveable with the other of said calf section and foot section, the brace including an elongate slot sized for receiving the pin, the pin being positionable within the slot, the position of the pin relative to the slot varying along the slot as said calf section is moved between its first and second positions.

13. An orthosis for elevating a patient's foot, the orthosis comprising a calf section configured for engaging a calf of the patient, and a foot section having a surface engageable portion, the foot section being operatively connected to the calf section for movement of the foot section between a retracted position in which the surface engageable portion is generally adjacent the foot of a patient wearing the orthosis, and a propping position in which the surface engageable portion is spaced generally rearwardly of the calf section for engaging a generally horizontal surface to elevate the patient's foot above the horizontal surface when the patient's foot is oriented with the back of the heel thereof facing generally downwardly.

14. The orthosis of claim 13 wherein the foot section is operatively connected to the calf section for pivotal movement of the foot section relative to the calf section between its retracted and propping positions.

15. The orthosis of claim 14 further comprising a locking mechanism configured for releasably locking the foot section in its retracted position.

16. The orthosis of claim 15 wherein the locking mechanism is configured for releasably locking the foot section in at least one position between its retracted and propping positions.

17. The orthosis of claim 16 wherein the locking mechanism comprises a brace operatively connected to and moveable with one of said calf section and foot section, and a pin operatively connected to and moveable with the other of said calf section and foot section, the brace including an elongate slot sized for receiving the pin, the pin being positionable within the slot, the position of the pin relative to the slot varying along the slot as said calf section is moved between its retracted and propping positions.

18. The orthosis of claim 17 wherein the pin and brace are configured for releasably locking the pin against the brace when the foot section is in any of its retracted position, propping position, and said one position.

19. The orthosis of claim 13 wherein the foot section has a generally convex upper surface engageable with the patient's foot when the patient is wearing the orthosis and when foot section is in its retracted position.

20. The orthosis of claim 13 wherein the surface engageable portion is generally adjacent the heel of the patient's foot when the patient is wearing the orthosis and when the foot section is in its retracted position.

21. The orthosis of claim 13 wherein the surface engageable portion constitutes a first surface engageable portion, the foot section further including a second surface engageable portion spaced from the first surface engageable portion, the first and second surface engageable portions being spaced generally rearwardly of the calf section for simultaneously engaging the generally horizontal surface to elevate the patient's foot above the horizontal surface when the patient's foot is oriented with the back of the heel thereof facing generally downwardly.

22. The orthosis of claim 21 wherein the first surface engageable portion is generally adjacent the heel of the patient's foot and the second surface engageable portion is generally adjacent the ball of the patient's foot when the patient is wearing the orthosis and when the foot section is in its retracted position.

23. The orthosis of claim 13 wherein the surface engageable portion is generally adjacent the ball of the patient's foot when the patient is wearing the orthosis and when the foot section is in its retracted position.

* * * * *